(12) United States Patent
Lihl et al.

(10) Patent No.: US 8,113,099 B2
(45) Date of Patent: Feb. 14, 2012

(54) APPARATUS FOR PROCESSING A SPECIMEN

(75) Inventors: Reinhard Lihl, Vienna (AT); Michael Zimmermann, Leopoldsdorf (AT); Andreas Hallady, Vienna (AT); Guenther Bock, Vienna (AT)

(73) Assignee: Leica Mikrosysteme GmbH, Vienna (AT)

( * ) Notice: Subject to any disclaimer, the term of this patent is extended or adjusted under 35 U.S.C. 154(b) by 929 days.

(21) Appl. No.: 11/940,413

(22) Filed: Nov. 15, 2007

(65) Prior Publication Data

US 2008/0118312 A1 May 22, 2008

(30) Foreign Application Priority Data

Nov. 17, 2006 (DE) .......................... 10 2006 054 609

(51) Int. Cl.
*B26D 5/16* (2006.01)

(52) U.S. Cl. .......................... 83/603; 83/915.5; 83/490

(58) Field of Classification Search .................. 82/70.1, 82/83, 86, 78; 83/915.5, 469, 490, 602; 409/97, 409/110, 125, 126, 130, 201, 237
See application file for complete search history.

(56) References Cited

U.S. PATENT DOCUMENTS

| | | | | |
|---|---|---|---|---|
| 554,333 A * | 2/1896 | Cook | | 409/110 |
| 953,904 A * | 4/1910 | French | | 409/144 |
| 1,095,399 A * | 5/1914 | Huntington | | 83/471.2 |
| 1,879,548 A * | 9/1932 | Sethman | | 409/199 |
| 2,068,199 A * | 1/1937 | Seletsky | | 408/16 |
| 2,143,241 A * | 1/1939 | Hallenbeck | | 33/710 |
| 2,429,464 A * | 10/1947 | Jearum | | 451/281 |
| 2,851,910 A * | 9/1958 | Muller et al. | | 269/58 |
| 3,351,047 A * | 11/1967 | Barker | | 408/17 |
| 3,626,783 A * | 12/1971 | Jagers | | 83/490 |
| 3,653,268 A * | 4/1972 | Diepeveen | | 74/55 |
| 3,715,946 A * | 2/1973 | Kaltenbach | | 83/72 |
| 3,771,405 A * | 11/1973 | Blum | | 83/714 |
| 3,894,671 A * | 7/1975 | Kulicke et al. | | 228/4.5 |
| 4,051,755 A * | 10/1977 | Raveed | | 83/167 |
| 4,489,633 A * | 12/1984 | van de Wouw | | 83/464 |
| 4,581,967 A * | 4/1986 | Ehm et al. | | 83/452 |
| 5,042,348 A * | 8/1991 | Brundage et al. | | 83/471.3 |
| 5,456,147 A | 10/1995 | Stange, Jr. | | |
| 6,276,990 B1 | 8/2001 | Greenland | | |

(Continued)

FOREIGN PATENT DOCUMENTS

DE  3923470 A1 * 1/1991

(Continued)

OTHER PUBLICATIONS

Buehler, Ltd., Product literature: "Buehler IsoMet 1000 Precision Sectioning Saw", FN00912 Rev. 2, 2005, Printed in U.S.A.

(Continued)

*Primary Examiner* — Kenneth E. Peterson
*Assistant Examiner* — Jennifer Swinney
(74) *Attorney, Agent, or Firm* — Hodgson Russ LLP (57) ABSTRACT

An apparatus (1) for processing specimens (15), comprising an observation device (2), a specimen holder (3) for receiving the specimen (15) to be processed, and a tool holder (6), the tool holder (6) being pivotable in a plane normal to its longitudinal axis (L') by a pivot arm (22), and being rotatable about its longitudinal axis (L'); furthermore a drive system for selectable execution of the pivoting of the pivot arm (22) is provided.

13 Claims, 8 Drawing Sheets

U.S. PATENT DOCUMENTS

| | | | |
|---|---|---|---|
| 7,039,548 B2 * | 5/2006 | Takano et al. | 702/151 |
| 7,059,229 B2 * | 6/2006 | Lanzer | 83/493 |
| 7,168,901 B2 * | 1/2007 | Ranner | 409/293 |
| 7,178,438 B2 * | 2/2007 | Xin et al. | 83/397 |
| 7,480,037 B2 * | 1/2009 | Palmateer et al. | 356/237.1 |
| 7,574,950 B2 * | 8/2009 | Hetcher et al. | 83/473 |
| 2002/0083812 A1 * | 7/2002 | Lanzer | 83/490 |
| 2004/0149110 A1 | 8/2004 | Kubota | |
| 2004/0246571 A1 * | 12/2004 | Bonaventura | 359/368 |
| 2004/0251434 A1 * | 12/2004 | Zimmermann et al. | 250/559.12 |
| 2005/0152760 A1 | 7/2005 | Ranner | |

FOREIGN PATENT DOCUMENTS

| | | |
|---|---|---|
| DE | 4123435 A1 * | 1/1992 |
| DE | 4030185 A1 | 3/1992 |
| DE | 19819144 C1 | 6/2000 |
| DE | 10257229 A1 | 6/2004 |
| DE | 10258555 A1 | 7/2004 |
| EP | 0997228 A1 | 5/2000 |
| JP | 02041856 A * | 2/1990 |
| JP | 2004009201 A | 1/2004 |
| JP | 2004009293 A | 1/2004 |
| WO | 2008014351 A1 | 1/2008 |

OTHER PUBLICATIONS

Leica Mikrosysteme Gmbh, "Leica EM Trim Operating Manual", Jan. 2000, Vienna, Austria.

European Patent Office Action, Mar. 22, 2010, in European Patent Application No. EP 07450125.

\* cited by examiner

APPARATUS FOR PROCESSING A SPECIMEN

CROSS-REFERENCE TO RELATED APPLICATIONS

This application claims priority of the German patent application no. 10 2006 054 609.1 filed Nov. 17, 2006, which is incorporated by reference herein.

FIELD OF THE INVENTION

The present invention relates to an apparatus for processing specimens, having an observation device for observing a specimen, a specimen holder for receiving the specimen to be processed, and a tool holder.

BACKGROUND OF THE INVENTION

Apparatuses of this kind are manufactured for the preparation of specimens, in particular for the production of microtome sections. For this, tissue specimens to be examined are, for example, embedded in synthetic resin and these specimens are processed by means of milling cutters into the shape of truncated pyramids. These trimmed specimens are then sectioned in a microtome, thereby yielding tissue sections having a thickness in the micrometer or nanometer range that can then be examined.

The assignee of the present application has developed a unit that is suitable for such tasks and is already on the market. This unit additionally comprises an observation device with which the specimen can also be observed during processing.

These units are not suitable, however, for specimens made of harder material. For example, semiconductor materials such as silicon, gallium arsenide, and the like cannot be milled; other tools, in particular saws, are necessary for them.

An automatic sawing apparatus is disclosed, for example, in U.S. Pat. No. 5,456,147, the specimen to be processed being mounted on a movable arm and being brought via a positive guidance system into contact with the saw wheel, which rotates about its axis but is otherwise mounted rigidly in the housing of the apparatus.

A disadvantage of such systems is that the specimen is moved during processing, and observation of the specimen during processing is therefore not possible. The positive guidance system can moreover, for example, impose too great an advance which causes undesirable tensile forces; this can negatively affect the quality of the cut and, in the worst case, result in destruction of the specimen. Complex monitoring devices that measure the pressure loads on the saw and specimen arm are therefore necessary in order to protect the specimen and/or the saw wheel.

SUMMARY OF THE INVENTION

It is therefore an object of the invention to create an apparatus of the kind cited initially that overcomes these disadvantages.

This object is achieved according to the present invention in that the tool holder is pivotable in a plane normal to its longitudinal axis by means of a pivot arm, and is rotatable about its longitudinal axis; and that a drive system for selectable execution of the pivoting of the pivot arm is provided. In this disclosure, the longitudinal axis of the tool holder is understood as that axis about which the tool that is inserted in the tool holder is rotatable. Because of the pivotability of the tool holder, the specimen can remain unmoved in the specimen holder, and the tool is moved in relation to the specimen. Because of the stationary positioning of the specimen the latter can, in contrast to the known existing art, also be viewed through the observation apparatus, for example a stereomicroscope, during processing. The pivotability of the tool holder defines the advance of the tool inserted in the tool holder, for example a saw. The rotatability of the tool holder about its longitudinal axis is necessary for driving the tools inserted in the tool holder.

When sawing specimens made of hard material, in particular specimens made of various materials having different hardness values, a uniform, controlled advance of the saw blade is of particular importance. In a variant of the apparatus according to the present invention, the pivot arm is acted upon by a weight displaceable along a guide, the force of the weight producing the pivoting of the pivot arm and thereby defining the advance of the tool.

In weight-guided systems such as, for example, the ISOMET 1000 Precisioning Sectioning Saw of Buehler Ltd. (cf. document "ISO Met 1000," "Precision Sectioning Saw," Buehler Ltd. USA, 25M0405, FN00912 Rev. 2, printing date 2005), the saw blade often comes to a standstill with very small advance values (<0.05 mm/s) because of the small applied weight and the differing friction between the saw blade and specimen caused by different materials.

Another possibility for adjusting the advance or the cutting speed is the use of a positive guidance system. In another variant of the invention, the advance of the tool is therefore implemented via a positive guidance system, for example a linear guidance system, the pivot arm being connected via a guidance element to a drive system whose drive motion produces the pivoting of the pivot arm.

In the case of specimens having a round cross section, the frictional surface of the saw blade and specimen changes with progress of the saw and/or the saw resistance changes due to different hardness values of the various materials within the specimen. With greater applications of weight the different material properties likewise result in irregular cutting speeds, which in turn negatively affects the surface quality of the cut. With positive guidance, problems often occur when the advance is too great or the saw is blunt, and in the worst case these result in breakage of the saw blade and/or of the specimen. In a preferred embodiment of the invention, weight application and positive guidance are therefore combined in such a way that the pivot arm is acted upon by a weight and is connected via a guidance element to a drive system, the guidance element comprising an articulated arm that connects the pivot arm to a lever that is acted upon by the weight that is displaceable along a guide.

The guidance element is preferably connected to the drive system via a linkage that is suitable for converting a rotational motion into a translating motion. A cam plate that is in releasable contact with the weight is preferably used as a linkage. The cam plate converts the rotational motion of the drive system into a translating motion of the lever. A spindle can also, for example, be used as a linkage. If the lever lags behind as the drive system moves in the manner determined by the drive system, for example because the tool's advance is being braked (possibly bringing the saw to a standstill) because of frictional forces between the saw and specimen, the connection between the guide element and drive system is then released. Only the weight is now acting on the pivot arm and the specimen, and none of the tensile forces produced by the positive guidance system can negatively affect the specimen and/or saw blade.

In a preferred embodiment of the invention, the contact between cam plate and weight is implemented via a ball bearing. The ball bearing is particularly suitable for this use because of the small frictional forces that occur with regard to the cam plate.

The drive system is suitably a stepper motor, which in a preferred embodiment of the invention drives the advance, i.e. the pivoting of the tool holder, in micrometer-scale steps.

The apparatus according to the present invention is suitable not only for the use of saws, but also for grinding or polishing wheels and milling cutters. When samples made, for example, of metal or plastic are milled, an advance is necessary in a direction parallel to the longitudinal axis of the tool holder. The pivot arm is therefore movable along the longitudinal axis of the tool holder.

The apparatus can be used for processing of specimens that are subsequently further processed or sectioned with a microtome or ultramicrotome.

A farther advantageous use of the apparatus is for sectioning or initial cutting of specimens for subsequent specimen examination with a microscope. The latter can be embodied, for example, as a light microscope, scanning electron microscope, or atomic force microscope.

BRIEF DESCRIPTION OF THE DRAWING FIGURES

The invention will be further explained below with reference to a non-limiting exemplifying embodiment with pertinent Figures, in which.

DETAILED DESCRIPTION OF THE INVENTION

Figure 1:
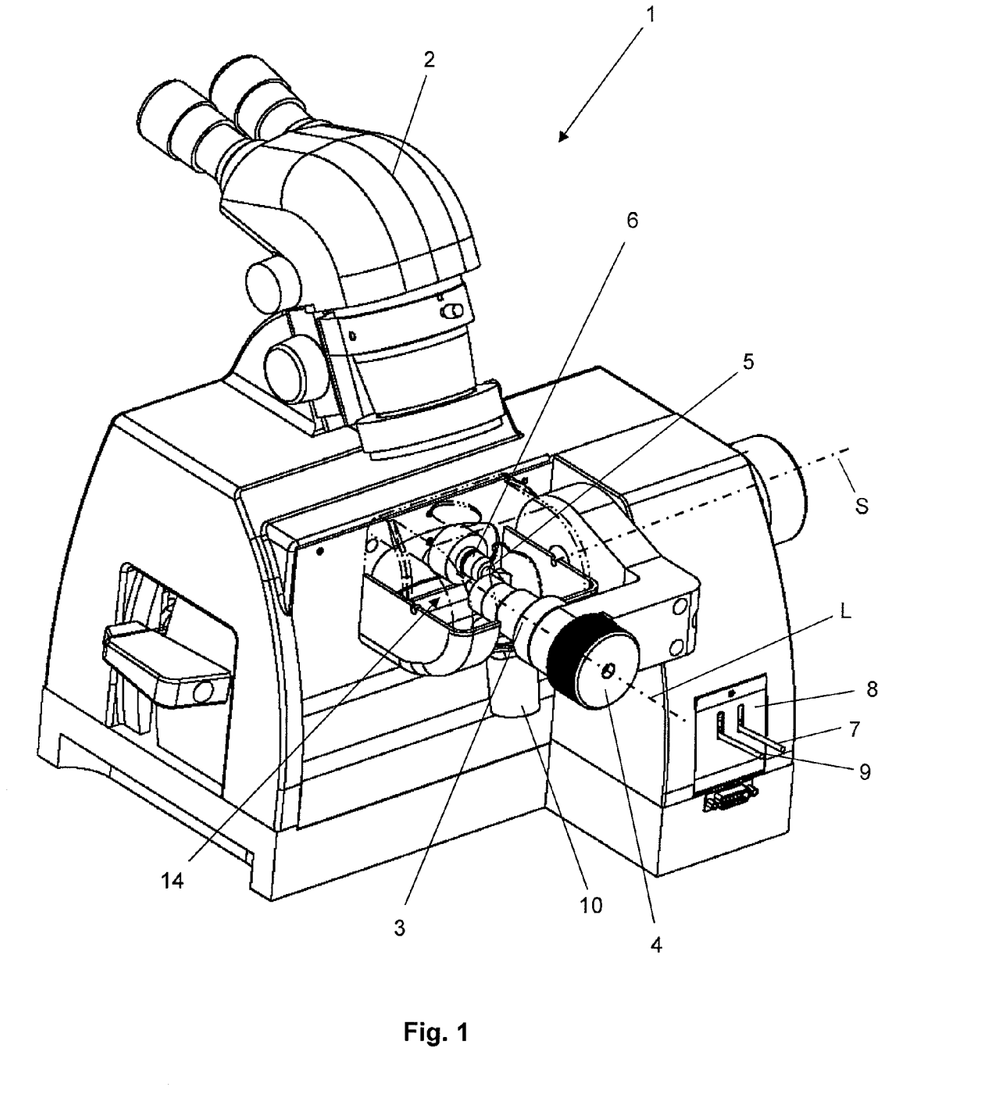
FIG. 1 is an oblique rear view of the apparatus from the upper right.

FIG. 1 is a first view of apparatus 1. Apparatus 1 comprises an observation device 2, for example a stereomicroscope, that serves for viewing of a sample to be processed, hereinafter called a "specimen." A measurement device that enables measurement of the specimen can be provided, if applicable, in the observation device. In a preferred variant of the invention, for example, there is inserted into the stereomicroscope a measuring eyepiece with which the specimen itself, but also the manner in which processing is progressing, can be accurately measured. Other systems such as, for example, video cameras and the like can also be used as observation device 2.

Apparatus 1 is equipped with a specimen holder 3 into which the specimen to be processed is inserted. The specimen by preference involves material of high hardness, for example semiconductor materials such as silicon, gallium arsenide, etc. The apparatus is, however, equally suitable for processing biological material that, favorably, is embedded in a synthetic resin.

Specimen holder 3, which is substantially of elongated conical shape, possesses a means for rotating the specimen about longitudinal axis L of specimen holder 3. The specimen can be rotated, by means of a rotary knob 4, in such a way that all regions of the specimen can be viewed through stereomicroscope 2 and/or edges of the specimen can be processed.

Tool 5, for example a milling cutter, is inserted into a tool holder, by preference into a clamping apparatus 6. In a preferred embodiment of the invention, clamping apparatus 6 is driven via a spindle. The rotation speed of the spindle is adjustable, for example, over a range from 300 to 20,000 revolutions per minute. The rotation speed range suitable for processing of the specimen depends on the nature of the specimen material, in particular on its hardness. Rotation speeds of approximately 20,000 rpm, for example, are usually required for milling, whereas for sawing or polishing, rotation speeds of 300-500 rpm often should not be exceeded in order to avoid damage to the specimen and to achieve the desired surface quality.

To allow the specimen to be cooled or lubricated during processing, a system is provided such that a coolant or lubricant is conveyed (from a reservoir that is not depicted) via a first inlet 7 to a pump 8, and is delivered via a second inlet 9 from pump 8 to the specimen. A suction device 10 is furthermore preferably provided in the region of the tool or specimen in order to remove coolant or lubricant, and the material removed during processing, from the specimen surface and from tool 5.

In a preferred variant of the invention, specimen holder 3 is pivotable about a pivot axis S. This pivotability of specimen holder 3 permits the specimen to be brought into a measurement position, a processing position, or an inspection position. FIG. 1 depicts the processing position, in which the longitudinal axes of specimen holder 3 and of clamping apparatus 6 are substantially parallel to one another.

Figure 2:
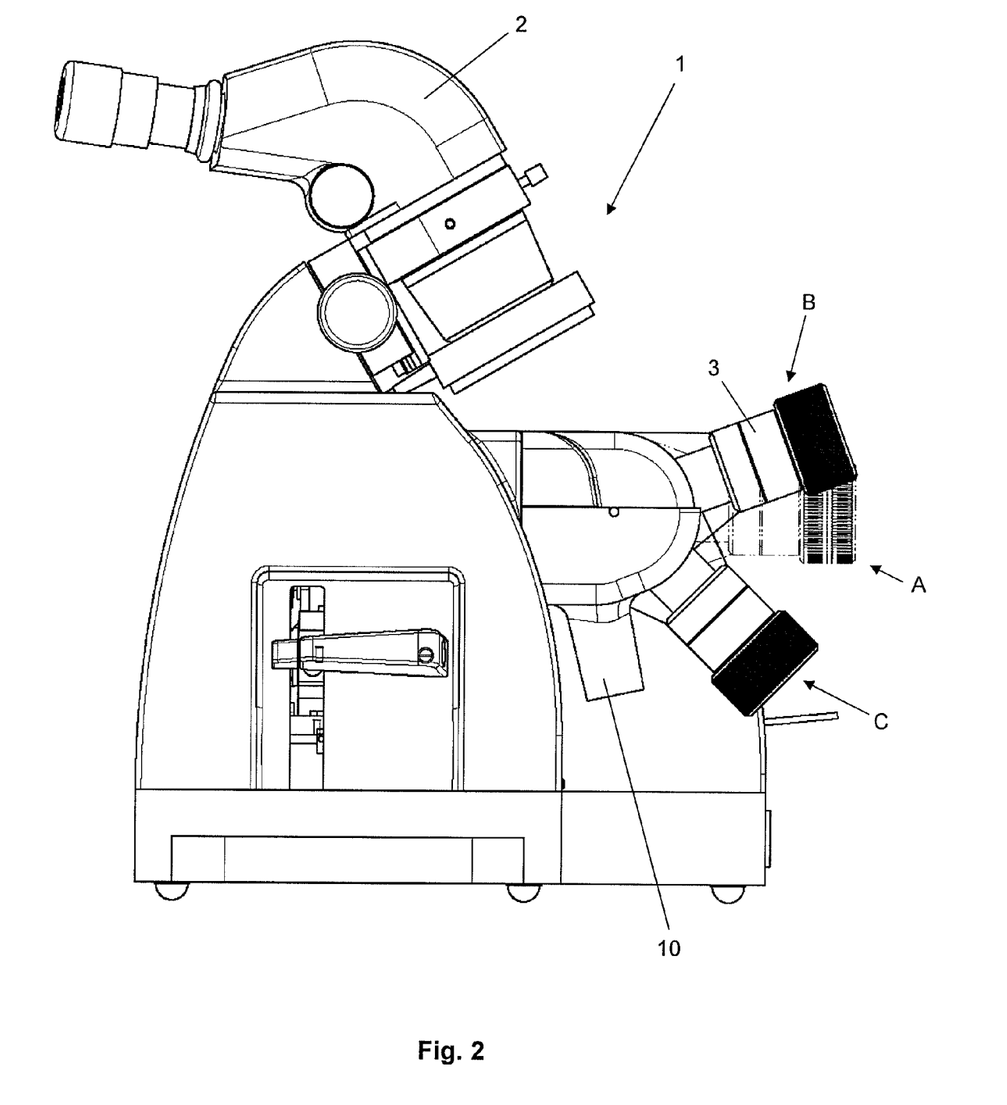
FIG. 2 is a side view of the apparatus of FIG. 1.

FIG. 2 depicts the three positions of specimen holder 3 that are usually selected. In this depiction, processing position A depicted in FIG. 1 is shown with dot-dash lines. In a measurement position B located approximately 20° above processing position A, accurate measurement of, for example, the specimen edges is possible using suitable measurement apparatuses in observation device 2. If, for example, a phase boundary in a specimen is being exposed by preparation for defect analysis, then firstly, for example, a small region of the specimen is milled down and the material removal required is then determined, for example by means of a measurement device in the eyepiece of microscope 2, by pivoting the specimen into measurement position B. The specimen is then brought back into processing position A by being pivoted, and the specimen is processed in the manner thereby ascertained. Observation of the specimen through microscope 2 during processing is also possible, but with no capability for carrying out accurate measurements.

In a third position (inspection position C), specimen holder 3 is pivoted approximately 45° downward from processing position A. Here the specimen surface is located exactly in the beam path of stereomicroscope 2. In this position C, for example, a check is made as to whether the surface quality of the processed sample is adequate. An analysis of the specimen surface using suitable detectors, for example infrared or fluorescence detectors, is likewise conceivable. Suitable excitation sources in observation device 2 are a prerequisite for this.

Thanks to this observation capability, the progress of specimen processing can be checked at any time during processing with no need to interrupt processing and remove the specimen from specimen holder 3.

Figure 3:
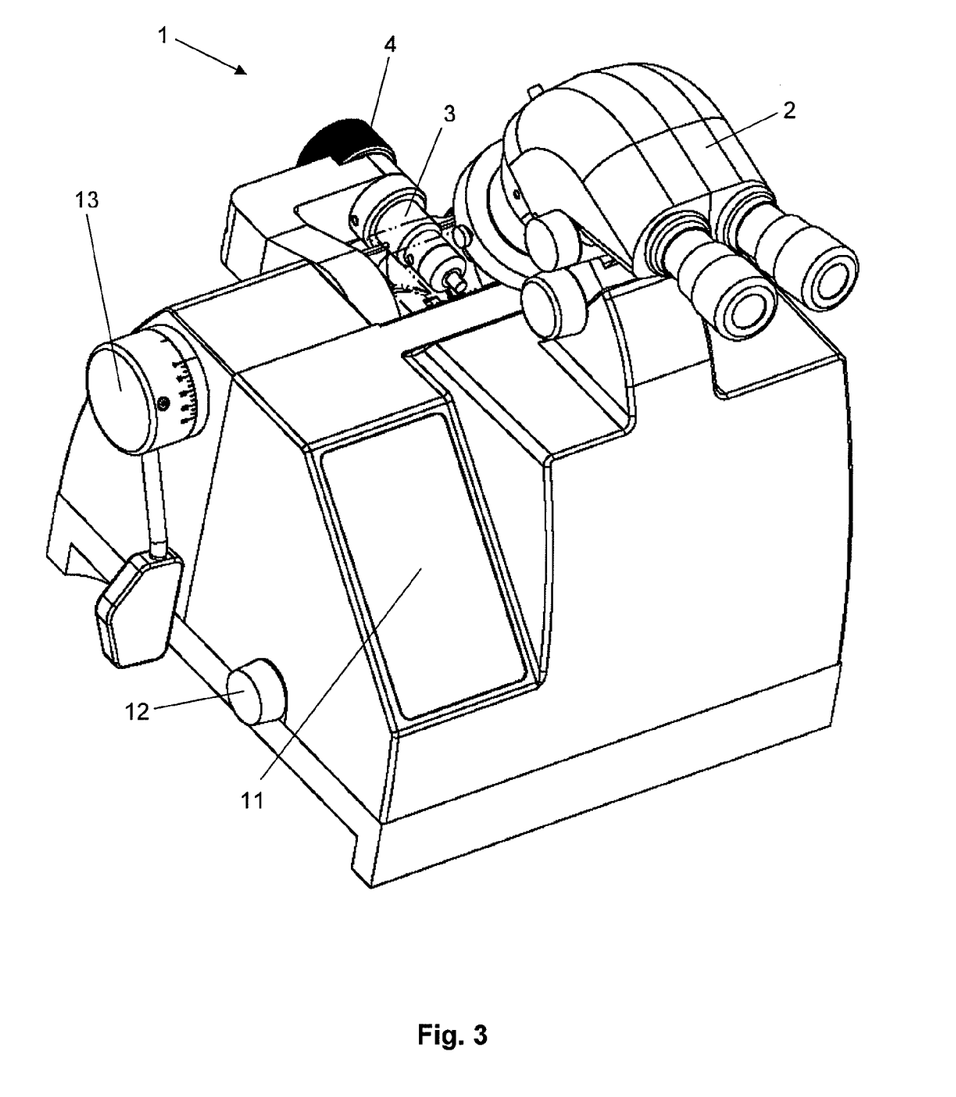
FIG. 3 is a front view of the apparatus of FIG. 1 from the upper left.

FIG. 3 is a front view of apparatus 1; from this side the user can view the specimen through stereomicroscope 2 and, via an input panel 11 that is embodied e.g. as a keypad with display or as a touch screen, can define all the parameters for processing the specimen, such as the rotation speed of tool 5. In the embodiment of invention as depicted, the advance of tool 5 is set via a rotary knob 12. In another variant of the invention, the advance is likewise defined via input panel 11.

Specimen holder 3 is pivoted via a setting wheel 13 in order to bring the specimen, as already mentioned above, into measurement position B or into the primary processing position A (FIG. 2). The primary processing position A is the position in which the specimen is usually processed, and in which the longitudinal axis of specimen holder 3 and the longitudinal axis of clamping apparatus 6 are aligned parallel with one another. Specimen holder 3 can also be brought into a position located between inspection position B and the primary processing position A. In this case the longitudinal axis of specimen holder 3 is inclined with respect to the longitudinal axis of clamping apparatus 6. It is thus possible to process the edges of the specimen at an angle corresponding to the angle of inclination enclosed by the longitudinal axes of specimen holder 3 and clamping apparatus 6.

Figure 4:
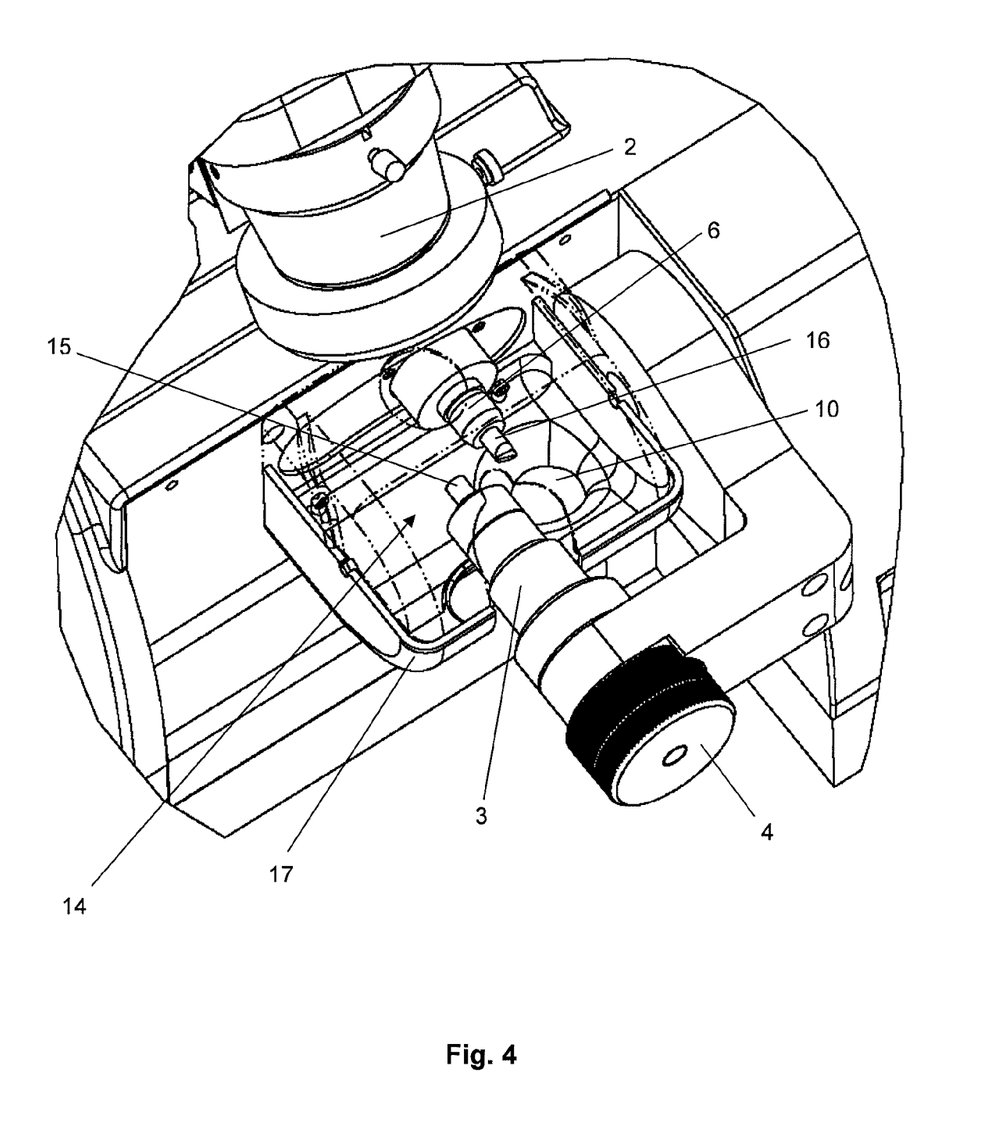
FIG. 4 is an enlarged detail view of the apparatus of FIG. 1 in the region of the clamping apparatus and the specimen receptacle, with a milling cutter.

An enlarged view of processing region 14 of apparatus 1 is shown in FIG. 4. A specimen 15 is mounted on specimen holder 3, which is rotatable by means of rotary knob 4. In the instance depicted, a milling cutter 16 is clamped in clamping device 6. In order to avoid contamination of the surrounding area and of apparatus 1 during processing of the specimen, processing region 14 is located in an at least partly transparent housing 17 that comprises a suction opening 10 through which the material removed during processing of specimen 15 is removed. This also avoids any contamination of the optics of stereomicroscope 2, and permits observation of specimen 15 during processing.

Figure 5:
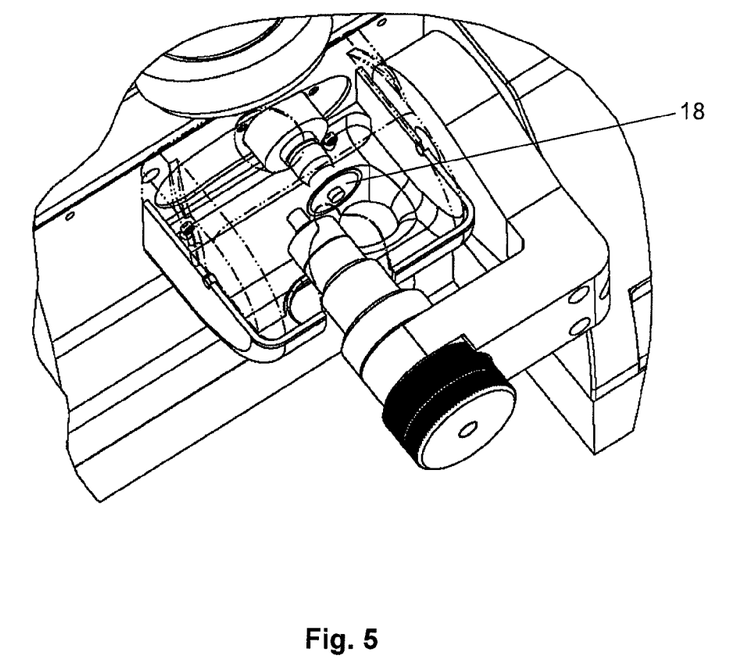
FIG. 5 is a view corresponding to FIG. 3, with a cutoff saw wheel.

FIG. 5 likewise shows processing region 14 with milling cutter 16 of FIG. 4 having been replaced by a saw wheel 18. This saw wheel is, for example, a diamond saw, making possible the sawing of particularly hard materials such as semiconductor materials.

Figure 6:
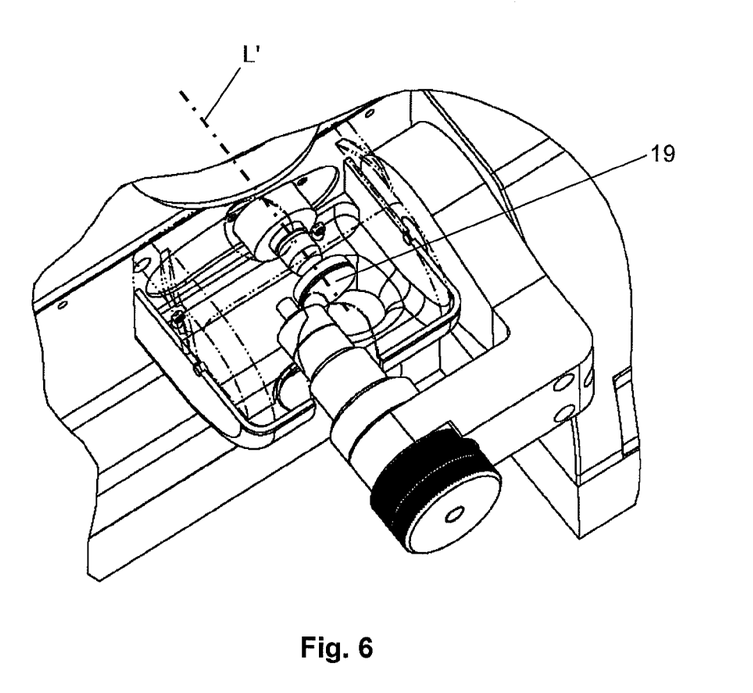
FIG. 6 is a view correspond to FIG. 3, with a polishing wheel.

In FIG. 6, instead of saw wheel 18 of FIG. 5, a grinding or polishing wheel 19 is inserted in the clamping apparatus 6 [sic].

Because higher temperatures occur during processing of the specimen, especially at higher spindle rotation speeds, and can impair the specimen surface or, in the worst case, destroy the specimen, in a preferred embodiment of the invention a system is provided for delivering coolant and/or lubricant. FIG. 7 once again shows processing region 14, saw 18 being secured in clamping apparatus 6. A metering tube 20 that is in communication with inlet 9 of pump 8 of FIG. 1 delivers the coolant or lubricant, which is applied directly onto specimen 15.

Figure 7:
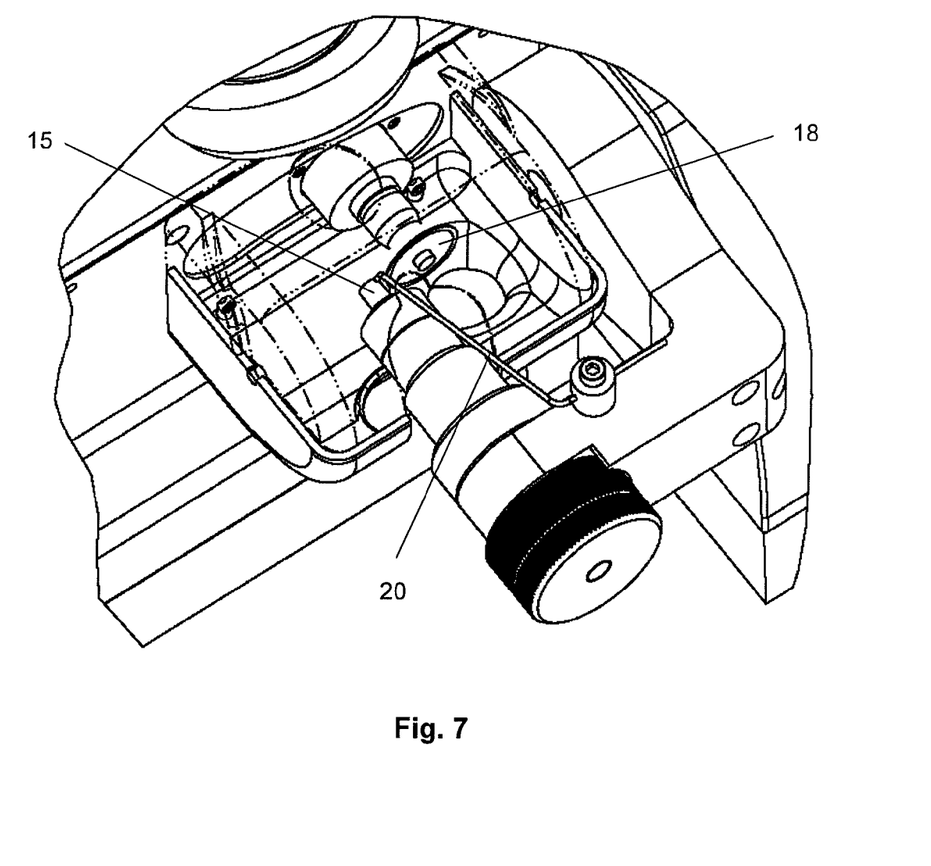
FIG. 7 is a view corresponding to FIG. 4, with an apparatus for lubrication during the sawing operation.

A delivery system of this kind can also be necessary in the context of milling or polishing; in the case of polishing of the specimen surface, for example, it is usual to use polishing agent, which is once again applied via metering tube 20 onto the specimen surface.

If, for example, a phase boundary in a semiconductor is to be examined in order to identify defects, specimen 15 is first inserted into specimen holder 3. By means of rotary knob 4, specimen 15 in specimen holder 3 is brought into the position provided for processing. After the insertion of, for example, saw 18, the specimen is first brought, with the aid of the pivotable specimen holder 3, into measurement position B that permits observation of the specimen edge. It is now possible to determine, by means of observation system 2, for example the measurement device in the stereomicroscope, how much material must be removed in order for the desired phase boundary to be exposed. Specimen holder 3 is then pivoted into processing position A, and processing, e.g. sawing, can begin.

A substantial advantage of apparatus 1 according to the present invention is that specimen 15 remains in specimen holder 3 both for measurement, e.g. for determination of the requisite processing depth, and also while the processing tools—such as milling cutter 16, saw 18, or polishing wheel 19—are being exchanged. As a result, specimen 15 remains without change in its position with respect to specimen holder 3, and reproducible results upon processing of specimen 15 are ensured. In contrast thereto, removal of specimen 15—for example for measurement in a separate observation device—and subsequent reinsertion of specimen 15 into specimen holder 3 often results in a discrepancy with regard to the original position of specimen 15 in specimen holder 3, so that a readjustment of specimen 15 in specimen holder 3, with additional effort, must be carried out. Especially when working on the micrometer scale, as in the present example, a shift in the specimen position can cause too much material to be removed, so that the desired phase boundary is missed during preparation. The processing results are therefore not satisfactory because of the positional discrepancy after the removal and reinsertion of specimen 15 into specimen holder 3. The same problem occurs if specimen 15 likewise needs to be removed from specimen holder 3 upon an exchange of tools.

The invention makes removal of the specimen superfluous, and high accuracy and reproducibility are guaranteed.

As specimen 15 is sawn, much of the material covering the phase boundary is removed. In this context, clamping apparatus 6 is moved in a plane normal to the rotation axis of tool holder 6 in accordance with the defined advance, and saw 18 is thereby guided through specimen 15. Depending on the nature of the material of specimen 15, coolant is brought via pump 8 and metering tube 20 to the specimen surface in the region of the saw cut, in order to avoid overheating of specimen 15 and/or of saw 18. During the sawing operation, specimen 15 can be observed at any time through stereomicroscope 2. The material occurring during sawing is continuously drawn off, if applicable together with the coolant or lubricant, in order to reduce contamination of processing space 14 and in particular of specimen 15.

Prior to exchange of the tool, specimen 15 in apparatus 1 according to the present invention can first be pivoted into inspection position C and the surface of specimen 15 can be checked. If no inspection of specimen 15 is necessary, specimen holder 3 remains in processing position A. The tool (in this case saw 18) is then removed from clamping apparatus 6 and replaced with polishing wheel 19, the specimen depth already removed being stored by a control unit of apparatus 1. Spindle 21 is usually displaced in the longitudinal axis in order to change tool 5, since tools 5 usually have different geometries. Polishing wheel 19 is then carefully displaced in longitudinal axis L' until contact is made against specimen 15, and further processing is then started. The previously sawn surface of specimen 15 is polished with the aid of this tool. The advance necessary during polishing is once again added by the control unit to the value, stored in the control unit, that has already been removed during sawing. The total amount removed from specimen 15 can thus be read out once the processing of specimen 15 is complete. Specimen 15 prepared in this fashion can now be examined, for example, with regard to defects.

Figure 8:
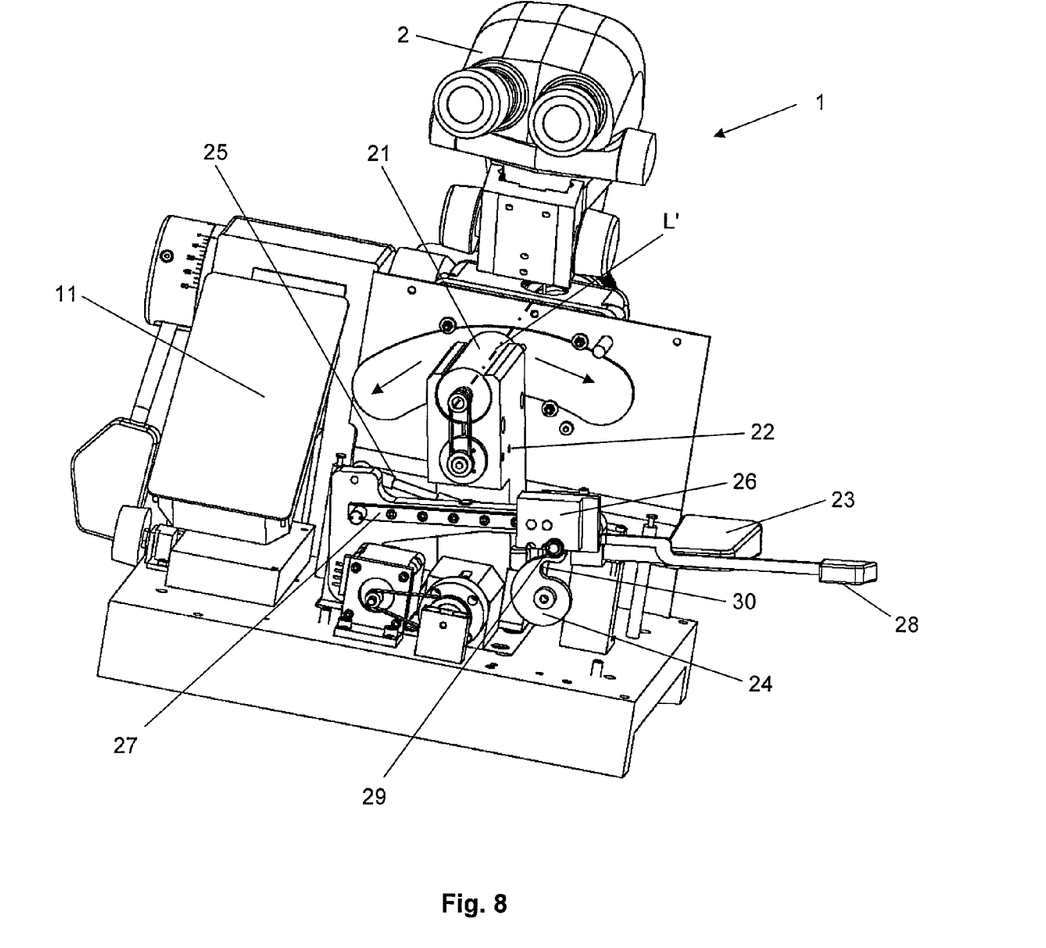
FIGS. 8 and 9 are each views of the apparatus according to FIG. 2 with the housing removed, with different cam plate positions.
Figure 9:
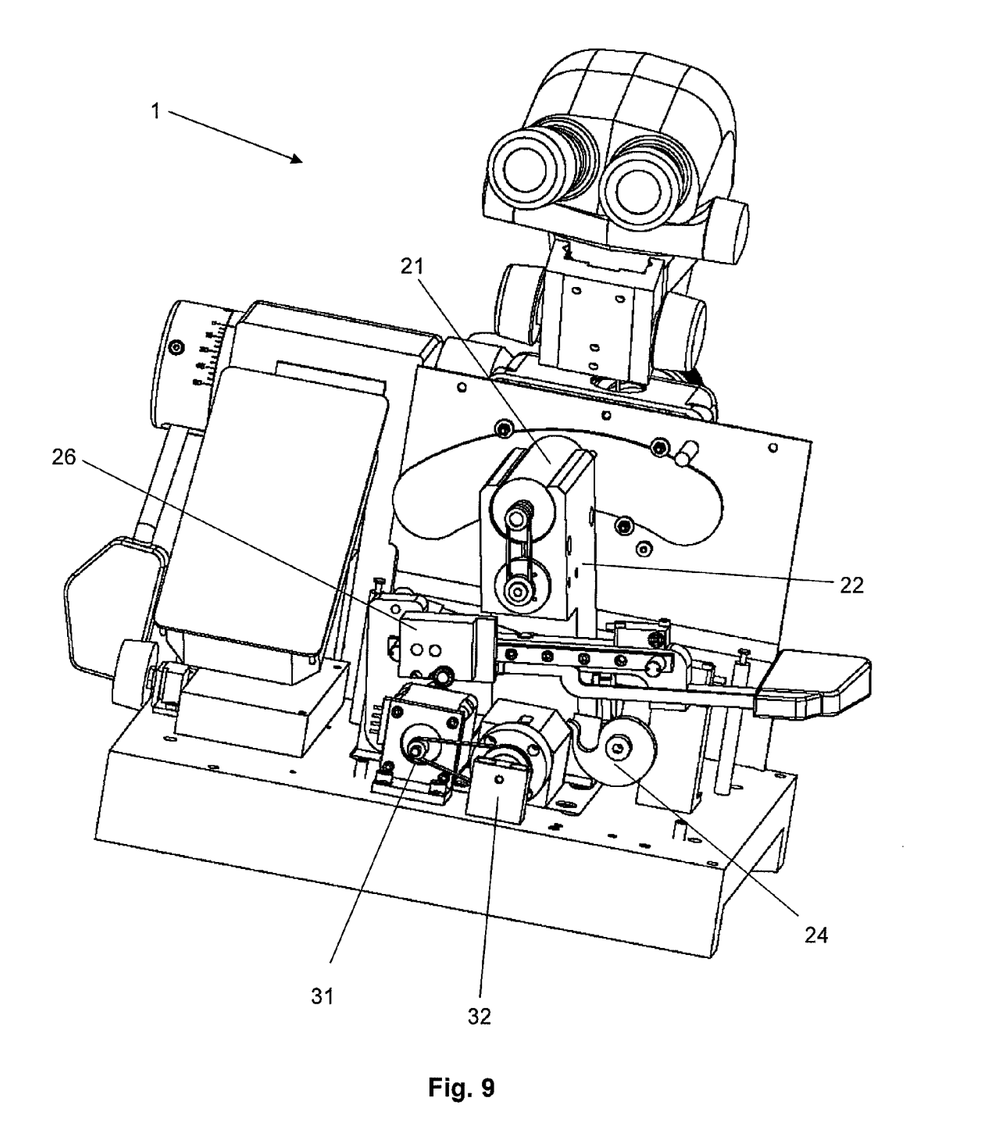

FIGS. 8 and 9 show a front view of apparatus 1 with the housing removed. The rotary motion of clamping apparatus 6 is implemented via a spindle 21. Spindle 21 is connected to a pivot arm 22, pivot arm 22 executing a pivoting motion (indicated by arrows) in a plane extending normal to the rotation axis of spindle 21.

When sawing specimens made of hard material, in particular specimens made of various materials having different hardness values, a uniform, controlled advance of the saw blade is of particular importance. It is useful to apply weights in order to adjust the advance, although this by itself does not yield a uniform advance because, for example, the frictional surface of the saw blade and specimen changes as sawing proceeds in specimens having a round cross section, or the saw resistance changes because of different hardness of the various materials within the specimen. With very small advance values (<0.05 mm/s), the saw blade often comes to a standstill because of the small applied weight and the differing friction between the saw blade and specimen caused by different materials. With greater applications of weight the different material properties likewise result in irregular cutting speeds, once again negatively affecting the surface quality of the cut. In addition, different cutting speeds can be set only by applying different weights. Another possibility for adjusting the advance or the cutting speed is the use of a positive guidance system. Here as well, problems often occur when the advance is too great or the saw is blunt, and in the worst case these result in breakage of the saw blade and/or of the specimen.

In the apparatus shown, a combination of positive guidance and weight application is implemented in order to establish a uniform cutting speed for saw 18. Pivot arm 22, and therefore the tool in clamping apparatus 6, is movable via lever 23 in a plane normal to longitudinal axis L' of spindle 21. This pivoting motion of pivot arm 22 defines the cutting speed of saw 18 and, in a preferred embodiment of the invention, is controlled via a stepper motor, the advance being adjustable, in particular, in the micrometer range.

The drive system, for example the stepper motor, is connected to lever 23 via a cam plate 24. Pivot arm 22 in turn is connected to lever 23 via a linkage rod 25 (positive guidance of pivot arm 22). Lever 23 is additionally acted upon by a weight 26, weight 26 resting on a guide 27 that is connected to lever 23. The force applied by weight 26 on lever 23, and therefore on pivot arm 22, changes depending on the location of weight 26. The effect of the weight is greatest when weight 26 is positioned, by movement of a slider 28, on the outer end of guide 27.

Cam plate 24 is in contact with weight 26 via a pin or, as in the embodiment shown, via a ball bearing 29. A ball bearing 29 is particularly suitable because of lower frictional forces. Cam plate 24, connected to the stepper motor, rotates clockwise in the embodiment of apparatus 1 that is shown. Because of the decreasing radius of cam plate 24, the rotation of cam plate 24 produces a lowering of weight 26, and thus of lever 23, at the speed predetermined by the drive system. As a result, pivot arm 22 moves to the right in FIG. 8. When cam plate 24 has performed an almost complete revolution about its own axis, ball bearing 29 travels into an indentation 30 of cam plate 24; the end point of the motion has thus been reached, and specimen 15 has been sawn through. Pivot arm 22 is thereupon pivoted back into its initial position (to the left in FIG. 8).

If saw blade 18 becomes stuck in the specimen, for example, pivot arm 22 thus cannot move further and lever 23 consequently remains in its present position. Cam plate 24 continues to rotate, and because of its decreasing radius loses contact with weight 26. The positive guidance of pivot arm 22 is thereby interrupted, and only weight 26 impinging on pivot arm 22 acts on specimen 15. Destruction of the specimen 15 and/or saw blade 18 by tensile forces resulting from a positive guidance system is thereby avoided. Once the end point of cam plate 24 is reached, pivot arm 22 is pivoted back into its initial position, and the stuck saw 18 is thus pulled out of specimen 15.

In another variant of the invention, the end point is defined not by arrival at the position of cam plate 24 in which ball bearing 29 enters indentation 30, but by stipulating a number of steps of the stepper motor that functions as the drive system. The number of steps can be entered, for example, via input panel 11.

If cam plate 24 is not in contact with weight 26, as shown in FIG. 9, no weight is then acting on pivot arm 22 and the latter is not connected to the drive system of cam plate 24. It therefore remains in the (manually) predetermined position. Tool 5 rotates as a result of the motion of spindle 21, with no advance. This zero-weight setting of pivot arm 22 is selected when apparatus 1 is used for processing a specimen 15 with milling cutter 16 or with grinding or polishing wheel 19.

When specimen 15 is being processed with milling cutter 16, or when grinding and polishing are being performed, it is often desirable for tool 5 to advance in a direction parallel to longitudinal axis L' of tool holder 6. This motion is generated by a spindle (not shown) in a drive system 31, which spindle acts directly or indirectly via a shaft 32 on pivot arm 22. This advance spindle has, for example, a pitch of 0.5 mm and is driven by a stepper motor at 400 steps per revolution.

In another embodiment (not depicted) of the invention, the positive guidance of pivot arm 22 is implemented by way of a linear guide that is pulled, by means of weight, onto an element that is displaceable at a controlled speed. Provision can also be made for spindle 21 comprising clamping apparatus 6 to be guided along a straight line and not, as shown previously, along a portion of a circular track. Cam plate 24 can moreover be replaced, for example, by a further spindle whose end serves as a support for pivot arm 22.

What is claimed is:

1. An apparatus for processing specimens comprising:
   an observation device for improving the observation of a specimen;
   a specimen holder for receiving the specimen to be processed; and
   a tool holder having a longitudinal axis about which the tool holder rotates relative to the specimen holder;
   a pivot arm connected to the tool holder, wherein the pivot arm is pivotable to move the tool holder in a plane normal to the longitudinal axis of the tool holder; and
   a drive system operable to pivot the pivot arm,
   wherein the pivot arm is acted upon by a weight mass and is connected to the drive system via a guidance element, the guidance element comprising an articulated arm that connects the pivot arm to a lever that is acted upon by the weight mass, and the weight mass being displaceable along a guide connected to the lever.

2. The apparatus according to claim 1, wherein the force of the weight mass produces the pivoting of the pivot arm.

3. The apparatus according to claim 1, wherein the guidance element is connected to the drive system via a linkage that is suitable for converting a rotational motion into a translational motion.

4. The apparatus according to claim 3, wherein the linkage is a cam plate that is in releasable contact with the weight mass.

5. The apparatus according to claim 4, wherein after the lever is left behind in the motion predetermined by the drive system, the connection between the guidance element and the drive system is released, and the weight mass continues to act on the pivot arm.

6. The apparatus according to claim 4, wherein the weight mass is in contact with the cam plate via a ball bearing.

7. The apparatus according to claim 4, wherein the drive system includes a stepper motor arranged to rotate the cam plate.

8. The apparatus according to claim 1, wherein the drive system includes a stepper motor.

9. The apparatus according to claim 1, wherein the movement of the tool holder is adjustable in micrometer-scale steps.

10. The apparatus according to claim 1, wherein the pivot arm is additionally movable along the longitudinal axis of the tool holder.

11. An apparatus for processing specimens comprising:
an observation device for improving the observation of a specimen;
a specimen holder for receiving the specimen to be processed; and
a tool holder having a longitudinal axis about which the tool holder rotates relative to the specimen holder;
a pivot arm connected to the tool holder, wherein the pivot arm is pivotable to move the tool holder in a plane normal to the longitudinal axis of the tool holder; and
a drive system operable to pivot the pivot arm,
wherein the pivot arm is acted upon by a weight mass and is connected to the drive system via a guidance element, the guidance element comprising an articulated arm that connects the pivot arm to a lever that is acted upon by the weight mass, and the weight mass being displaceable along a guide connected to the lever; and
wherein the observation device is a microscope.

12. The apparatus according to claim 11, wherein the observation device is a stereomicroscope.

13. The apparatus according to claim 11, wherein the pivot arm is additionally movable along the longitudinal axis of the tool holder.

* * * * *